United States Patent
Glazer et al.

(10) Patent No.: US 8,685,051 B2
(45) Date of Patent: Apr. 1, 2014

(54) CAPSULOTOMY DEVICES AND METHODS

(75) Inventors: Liane Clamen Glazer, Chestnut Hill, MA (US); Paul Glazer, Chestnut Hill, MA (US); Lawrence Crainich, Charlestown, NH (US); Drew Pickering, Jr., Shelton, CT (US)

(73) Assignee: Ojo, LLC, Chestnut Hill, MA (US)

( * ) Notice: Subject to any disclaimer, the term of this patent is extended or adjusted under 35 U.S.C. 154(b) by 109 days.

(21) Appl. No.: 13/092,696

(22) Filed: Apr. 22, 2011

(65) Prior Publication Data

US 2011/0264130 A1     Oct. 27, 2011

Related U.S. Application Data

(60) Provisional application No. 61/326,692, filed on Apr. 22, 2010.

(51) Int. Cl.
    *A61F 9/00*     (2006.01)

(52) U.S. Cl.
    USPC ........................................................ 606/166

(58) Field of Classification Search
    USPC .......... 606/107, 166, 170, 180; 623/6.12, 905
    See application file for complete search history.

(56) References Cited

U.S. PATENT DOCUMENTS

| | | | |
|---|---|---|---|
| 4,708,138 A | 11/1987 | Pazandak | |
| 4,766,897 A | 8/1988 | Smirmaul | |
| 5,135,530 A | 8/1992 | Lehmer | |
| 5,522,829 A * | 6/1996 | Michalos | 606/170 |
| 5,728,117 A | 3/1998 | Lash | |
| 5,792,166 A | 8/1998 | Gordon et al. | |
| 5,860,994 A | 1/1999 | Yaacobi | |
| 6,165,190 A | 12/2000 | Nguyen | |
| 6,551,326 B1 | 4/2003 | Van Heugten et al. | |
| 6,569,175 B1 * | 5/2003 | Robinson | 606/166 |
| 6,629,980 B1 | 10/2003 | Eibschitz-Tsimhoni | |
| 7,011,666 B2 | 3/2006 | Feinsod | |
| 7,763,032 B2 | 7/2010 | Ellis | |
| 2009/0157109 A1 * | 6/2009 | Bare et al. | 606/166 |
| 2011/0029005 A1 * | 2/2011 | Van Dalen et al. | 606/166 |

\* cited by examiner

*Primary Examiner* — Thomas McEvoy
(74) *Attorney, Agent, or Firm* — Edwards Wildman Palmer LLP; Joshua L. Jones

(57) ABSTRACT

An Anterior Capsule Remover ("ACR") device allows an ophthalmologist to safely and efficiently remove an anterior portion of the lens capsule at the beginning of cataract surgery. The device allows the surgeon to safely, efficiently and consistently create a circular central opening of a predetermined diameter in the top of the lens capsule. An exemplary anterior capsule remover apparatus includes a handle and a distal shaft that holds a blade or cutter. One or more o-rings attached to a thumbwheel and to the blade allow the surgeon to easily create a circular, central opening in the anterior capsule of predetermined diameter.

5 Claims, 18 Drawing Sheets

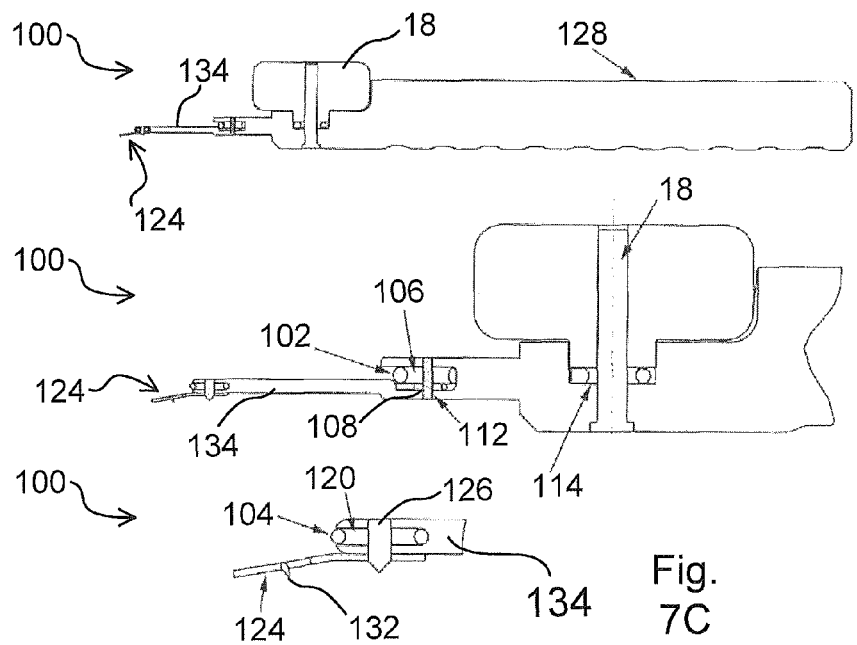
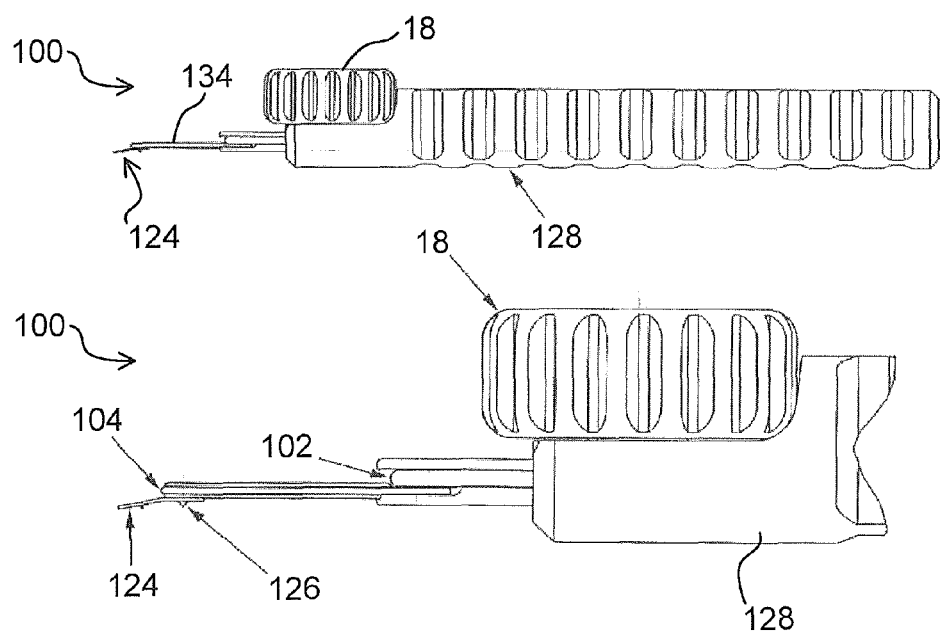

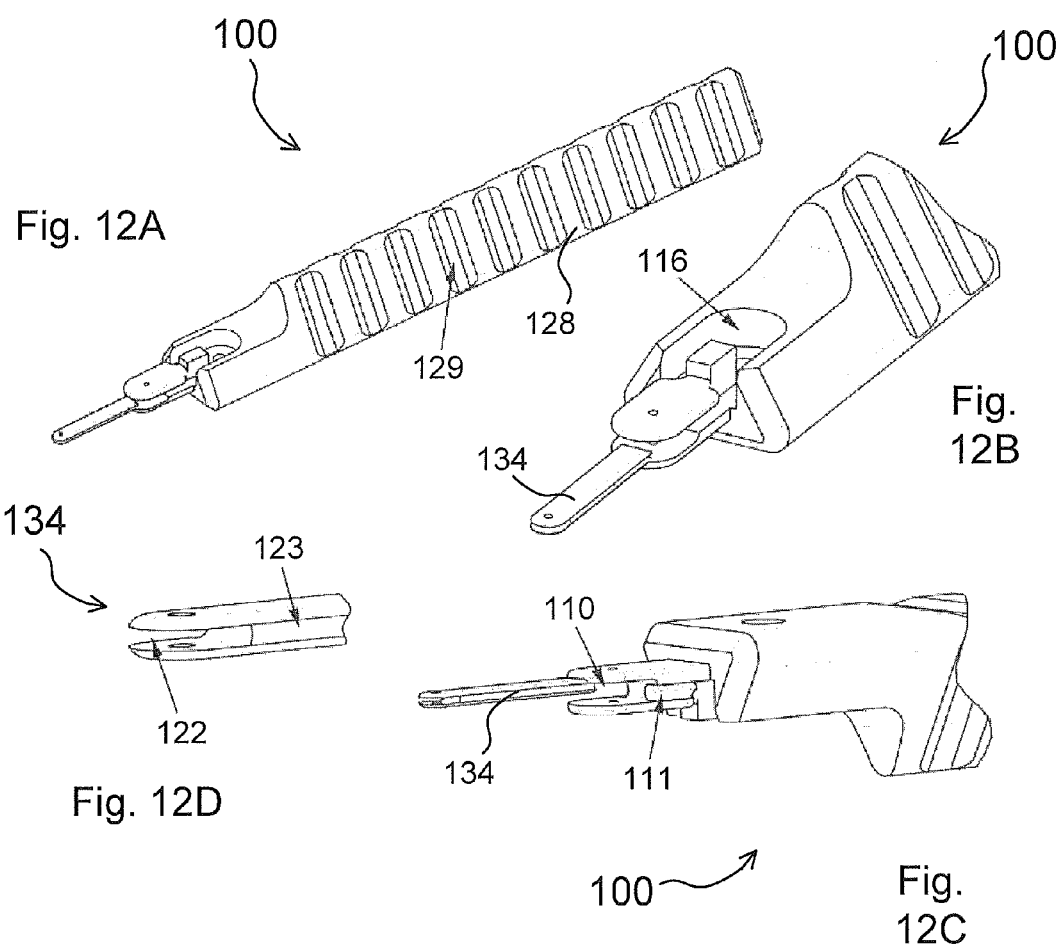

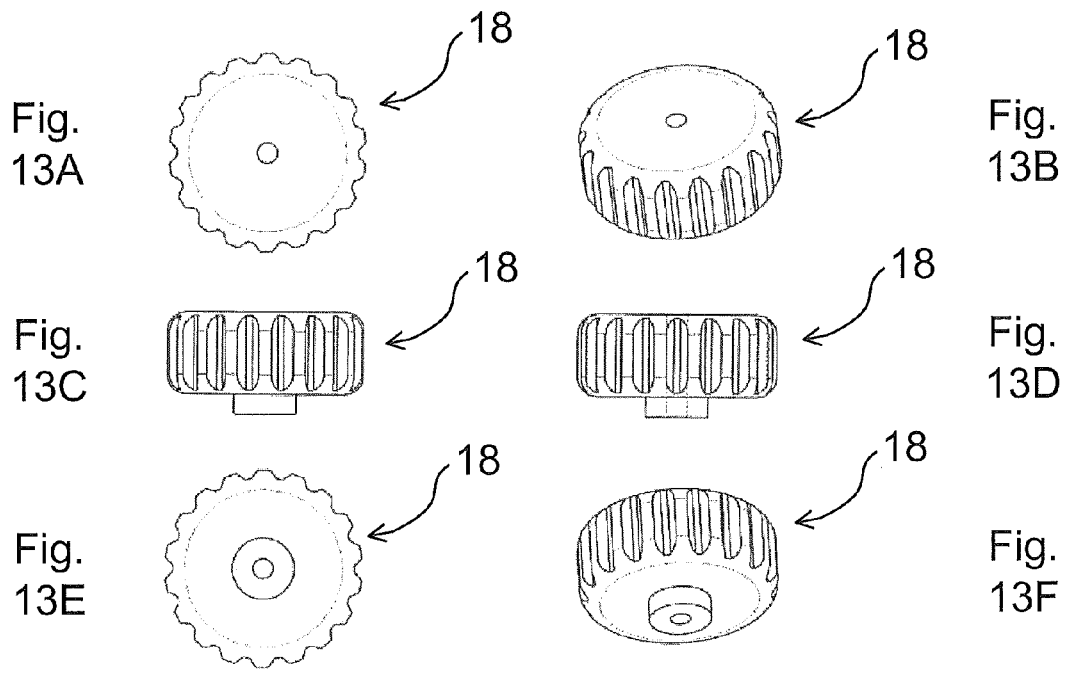
Fig. 13A  Fig. 13B
Fig. 13C  Fig. 13D
Fig. 13E  Fig. 13F
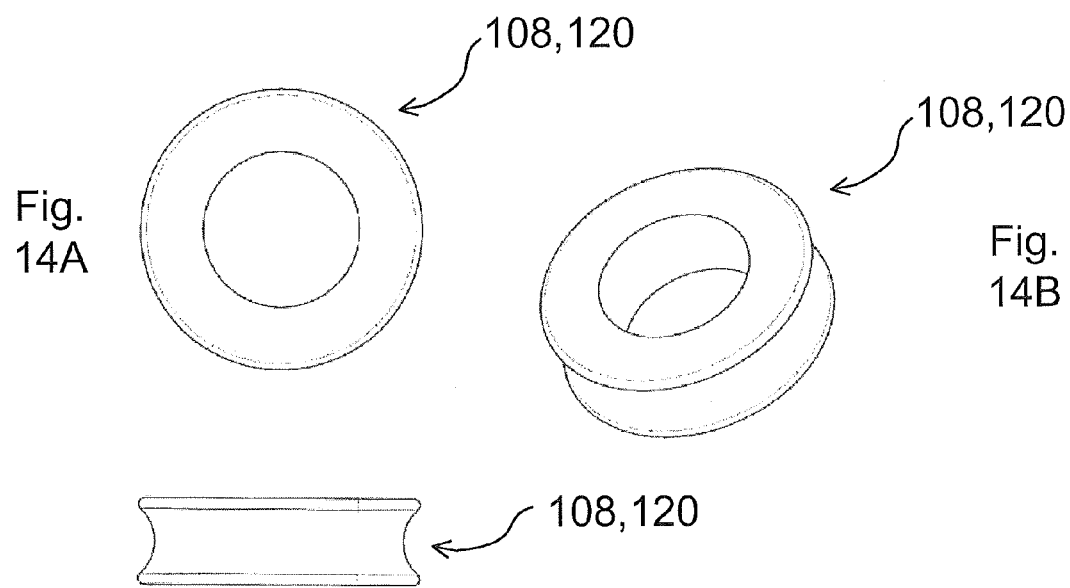
Fig. 14A  Fig. 14B
Fig. 14C

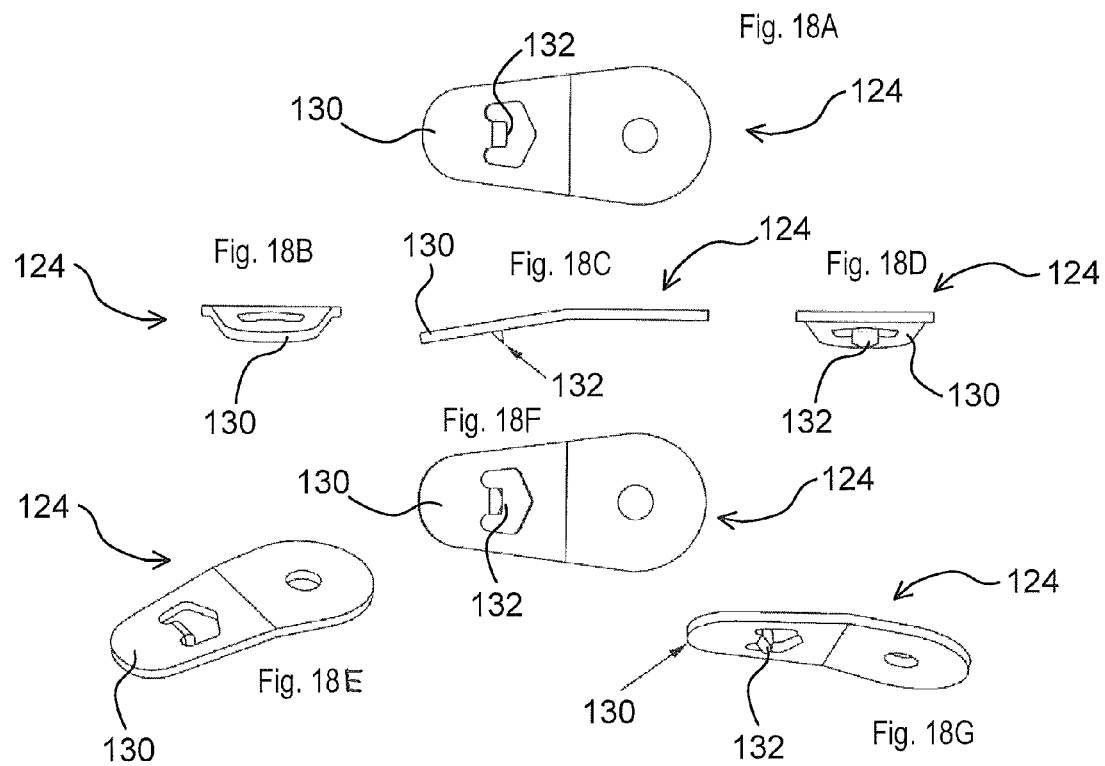
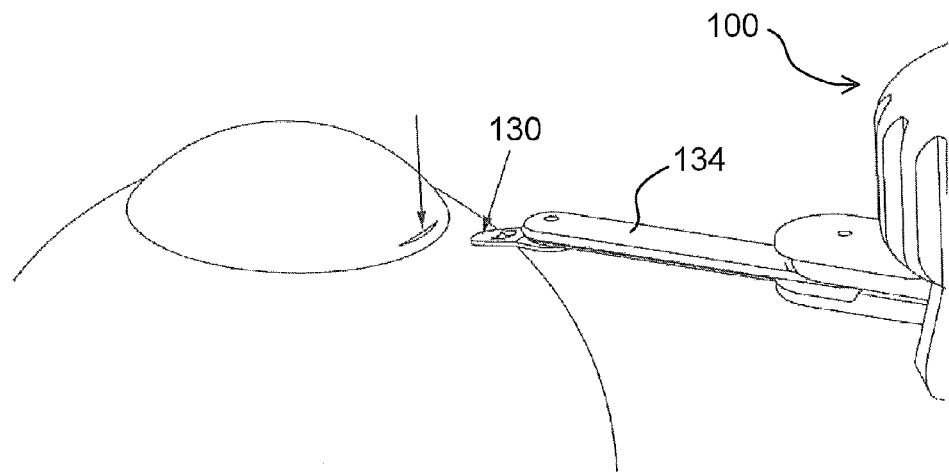

CAPSULOTOMY DEVICES AND METHODS

CROSS-REFERENCE TO RELATED APPLICATIONS

This application claims priority to U.S. Provisional Patent Application Ser. No. 61/326,692 filed Apr. 22, 2010 entitled "Anterior Capsule Removal Device to Assist with Capsulotomy Creation During Cataract Surgery." The foregoing provisional application is incorporated by reference herein in its entirety as if repeated herein.

BACKGROUND OF THE INVENTION

1. Field of the Invention

The present invention relates to instruments and methods for creating an incision in an intraocular tissue, and more particularly to instruments and methods for creating an incision in the anterior capsule of the eye.

2. Description of Related Art

The function of the human eye is to provide vision by allowing an image to be focused on the retina, which then transports the image via the optic nerve to the brain. In order to focus the image on the retina, there are refracting units in the eye: the eye uses the power of the clear cornea (which adds approximately 43 Diopters of plus power to the eye), and the crystalline lens (which adds 15-20 D of power) to focus an image on the retina, in the back of the eye. The quality of the focused image depends on a variety of factors, including the size and shape of the eye as well as the transparency of the cornea and the lens. A healthy human lens is transparent and biconvex, encapsulated by an elastic basement membrane composed of collagen and attached to the ciliary muscles via zonular fibers. Age, disease or trauma can damage the lens, causing the lens to become less transparent. The lens is then called a cataract. A cataract impairs vision by changing the refractive index of the lens, scattering light rays, and reducing the transparency of the lens. This condition is currently treated by surgically removing the cataract and replacing the impaired lens with an artificial intraocular lens (IOL).

Currently, in the United States, most cataractous lenses are removed using a surgical technique called phacoemulsification. During this type of cataract surgery, a viscoelastic substance is injected into the eye through a small corneal incision of approximately 1.5 mm (the side or "paracentesis" port) to maintain the depth of the anterior chamber. A larger (2-3 mm) incision is then made at the limbus of the eye (where the cornea meets the sclera) or on the edge of the cornea itself. A capsulotomy, as described in detail below, is performed to create a circular central opening in the anterior capsule. The thin phacoemulsification cutting tip is then inserted through the limbal incision, through the opening in the anterior capsule, and into the cataract in order to remove the cataract. After the cataract has been removed, an artificial IOL is slipped through the opening in the anterior capsule, and into the remaining capsular bag.

The creation of a circular central opening in the anterior capsule (a capsulotomy) is a necessary step in cataract surgery that serves two purposes: it allows the surgeon access to the lens so that the cataract can be removed, and it also allows the surgeon to place a posterior chamber intraocular lens (PCIOL) into the capsular bag. The capsulotomy is often the most difficult step in cataract surgery for the novice surgeon to master. Even seasoned surgeons sometimes encounter problems with this step.

Currently, the two most popular techniques for anterior capsulotomy are the "can-opener" technique and the capsulorrhexis. In a can-opener capsulotomy, a needle or a cystotome is inserted through the limbal or corneal incision, and small tears are made in the anterior lens capsule in a circular pattern. When a complete circle has been created, the cystotome or needle is removed from the eye and forceps are introduced into the eye. The center of the anterior capsule is then grasped with forceps and torn away along the perforations. Unfortunately, this procedure of opening the capsule with numerous small capsular tears creates small tags which become a focal area of least resistance and can lead to tears which extend radially and posteriorly to the posterior capsule. Radial tears in the capsule can result in complications, as described above.

The capsulorrhexis is the more commonly used method for the creation of the circular central opening in the anterior capsule. In a capsulorrhexis procedure, a cystotome is inserted into the eye and used to create the initial tear in the anterior capsule. This first tear is made near the center of the eye to increase the distance of the initial flap from the lens equator. In the next step of the capsulorrhexis procedure, either the cystotome or a forceps is used to delicately manipulate the free flap in a circular motion to peel a continuous circular tear in the anterior capsule. This procedure is difficult to control by the surgeon. It is often difficult to visualize the thin capsule (the capsule varies from 2-28 micrometers in thickness, and is thinnest at its anterior and posterior poles). The edge of the capsulorrhexis is particularly difficult to visualize in a dense subcapsular cataract where the red reflex may be absent. In these cases, the surgeon may feel the need to inject a dye such as 10% sodium fluorescein into the eye to stain the capsule and enhance the view of the rhexis. In addition, the tearing motion can lead to a radial tear (an undesirable tear toward the equator and the posterior capsule). Finally, the opening size and position is very hard to control. A capsulotomy that is too small can make the remainder of the surgery very difficult to perform. In addition, small capsular openings tend to seal and form fibrous proliferation, thereby causing glare for the patients post-operatively. Due to the above factors, the capsulorrhexis is widely considered to be one of the most difficult steps in cataract surgery.

If a radial tear occurs during the creation of a capsulotomy, the tear may extend to the posterior capsule, and increase the risk of complications. These complications can include loss of integrity of the capsule, requiring the implantation of a lens other than the preferred PCIOL. Another complication due to a radial tear is vitreous entry into the anterior chamber. In addition, a posterior capsule tear could allow entry of the entire cataract or of pieces of the lens into the posterior chamber, requiring a vitrectomy, and placing the patient at an increased risk of damage to the retina. A capsulotomy that results in a tear of the capsule increases operative time and patient discomfort. It also increases the likelihood of a bad visual outcome for the patient.

The following patents, each of which is incorporated by reference herein in its entirety, are found to be related to the field of surgical apparatus used in the capsulotomy step of cataract surgery:

1. U.S. Pat. No. 5,728,117 issued to Lash on Mar. 17, 1998 for "Retractable Capsulorrehexis Instrument".
2. U.S. Pat. No. 6,629,980 issued to Eibschitz-Tsimhoni on Oct. 7, 2003 for "Instrument And Method For Creating An Intraocular Incision".
3. U.S. Pat. No. 6,551,326 issued to Van Heugten, et al. on Apr. 22, 2003 for "Capsulorrhexis Device".
4. U.S. Pat. No. 7,011,666 issued to Feinsod on Mar. 14, 2006 for "Incising Apparatus For Use In Cataract Surgery".

5. U.S. Pat. No. 4,766,897 issued to Smirmaul on Aug. 30, 1988 for "Capsulectomy Surgical Instrument".

6. U.S. Pat. No. 5,135,530 issued to Lehmer on Aug. 4, 1992 for "Anterior Capsular Punch With Deformable Cutting Member."

7. U.S. Pat. No. 7,763,032 issued to Ellis on Jul. 27, 2010 for "Method and apparatus for forming an aperture in a lens capsule of an eye."

8. U.S. Pat. No. 5,792,166 issued to Gordon on Aug. 11, 1998 for "Anterior capsulotomy device and procedure."

Such conventional methods and systems have generally been considered satisfactory for their intended purpose. However, there is still a need in the art for devices and methods that allow for improved capsulotomy. There also remains a need in the art for such devices and methods that are easy to make and use. The present invention provides a solution for these problems.

SUMMARY OF THE INVENTION

The subject invention is directed to new and useful devices and methods for improved capsulotomy. In one embodiment in accordance with the present disclosure, an instrument includes a handle with a distally extending shaft which supports a movable blade at the distal end of the shaft. A knob supported on the handle may be used to actuate the blade to cut an opening in the anterior capsule. Optionally, a shroud covers the cutting edge of the blade during insertion and removal of the device from the eye.

In certain embodiments the knob is a thumb wheel, and is connected to and actuates a thumb wheel pulley. A first o-ring is disposed in a groove about the thumb wheel pulley and, in turn, also is disposed around a drive pulley disposed at an intermediate point along the distally extending shaft. The drive pulley is connected to and drives a blade o-ring that extends distally from the drive pulley to the blade mechanism. The blade o-ring, in turn, is disposed around a blade pulley that is connected to the blade. Actuation of the thumb wheel knob by the user causes rotation of the thumb wheel pulley which drives the drive o-ring. The drive o-ring rotates the drive pulley which, in turn, drives the blade o-ring. As the blade o-ring causes the blade pulley to rotate, the cutting blade which is secured relative to the blade pulley rotates through an arc suitable for cutting the anterior capsule to form a capsulotomy. While the devices above have are described herein with the exemplary context of o-rings, those skilled in the art will readily appreciate that any suitable elastomeric body can be used without departing from the spirit and scope of the invention. For example, it is not necessary for the elastomeric body to have a circular cross-section.

In accordance with certain methods of the present disclosure, the distal end of the device which supports the blade is inserted through an incision, such as at the limbus of the eye, into the anterior chamber of the eye and the blade is approximately centered over the lens of the eye. The blade is pressed against the capsular bag until the blade cutting edge penetrates through the anterior capsule. The thumb wheel is activated to rotate the cutting blade and form the opening in the capsular bag. In one embodiment, the method includes rotating the blade in one direction slightly over 180° (e.g. about 190°), returning the blade to center, and then rotating the blade approximately the same arc of travel in the opposite direction to complete the circular incision. In such a method, a double sided blade can be used to cut in each direction. It is also contemplated that the blade can be rotated 360° in a single direction, in which case a single edged blade is sufficient.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein:

FIGS. 7A-7C are cross-sectional side elevation views of the instrument of FIG. 5, showing the handle portion, thumbwheel portion, and blade portion, respectively;

FIGS. 8A-8B are side elevation views of the instrument of FIG. 5, showing the handle portion and thumbwheel portions, respectively;

FIGS. 12A-12D are perspective views of portions of the instrument of FIG. 5, showing the grip, thumbwheel pocket, driver o-ring groove, and blade pulley pocket, respectively;

FIGS. 13A-13F are views of the thumb wheel of the embodiment of FIG. 5, showing the thumb wheel in top, top perspective, side elevation, side elevation with interior features, bottom, and bottom perspective views, respectively;

FIGS. 14A-14C are plan, perspective, and side elevation views, respectively, of the thumb wheel pulley of the instrument of FIG. 5;

FIGS. 18A-18G are top, front, side elevation, rear, upper perspective, bottom, and lower perspective views, respectively, of the blade of the instrument of FIG. 5;

FIG. 19 is a perspective view of the instrument of FIG. 5, showing the instrument in use with the distal tip approaching an incision in the limbus of the eye;

DETAILED DESCRIPTION OF THE PREFERRED EMBODIMENTS

Figure 1:
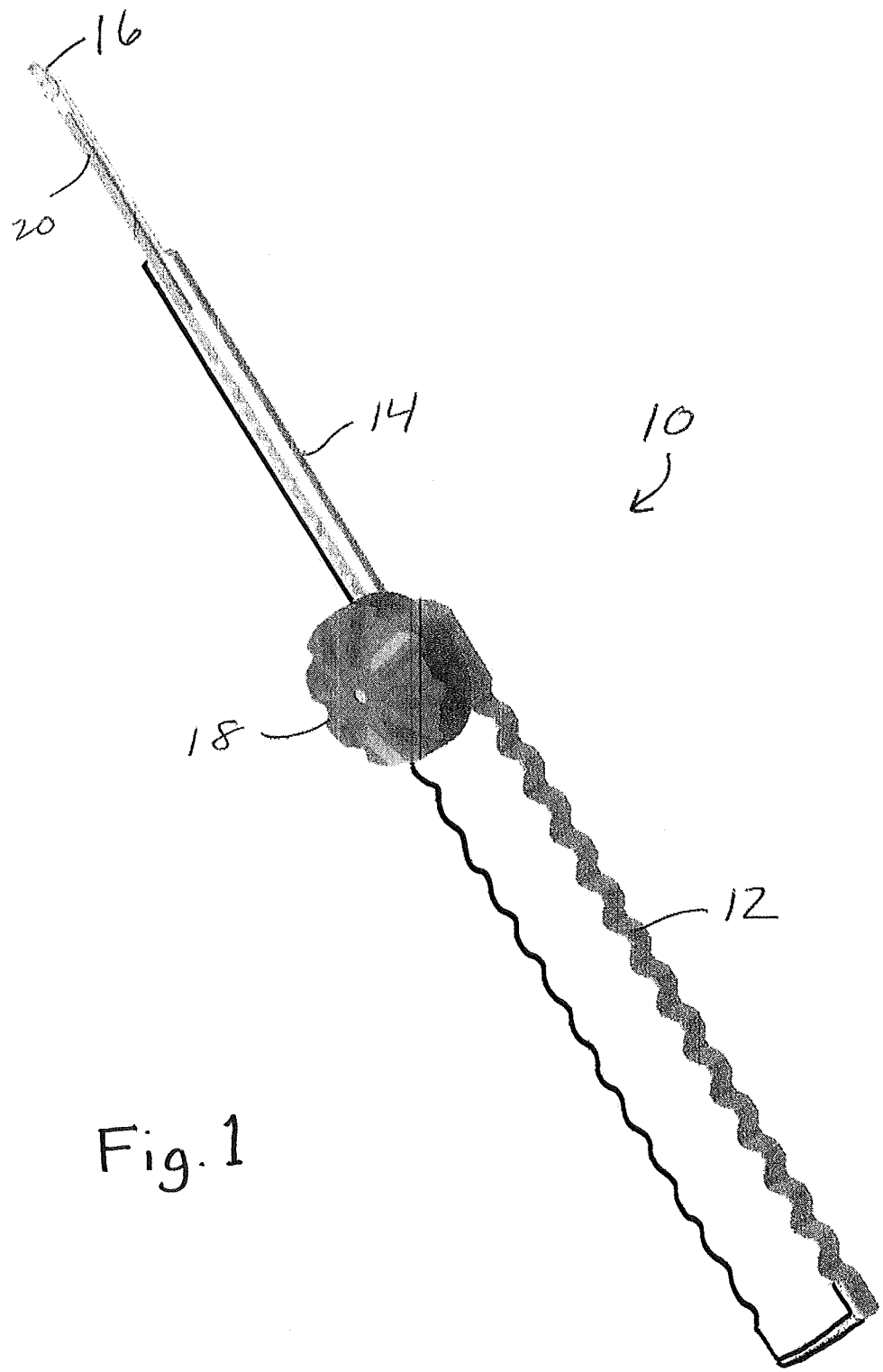
FIG. 1 is a perspective view of an exemplary embodiment of an instrument constructed in accordance with the present invention, showing the handle and distal tip thereof.

Reference will now be made to the drawings wherein like reference numerals identify similar structural features or aspects of the subject invention. For purposes of explanation and illustration, and not limitation, a partial view of an exemplary embodiment of an instrument in accordance with the invention is shown in FIG. 1 and is designated generally by reference character 10. Other embodiments of instruments in accordance with the invention, or aspects thereof, are provided in FIGS. 2-23, as will be described. The system of the invention can be used for capsulotomies and the like.

Figure 2:
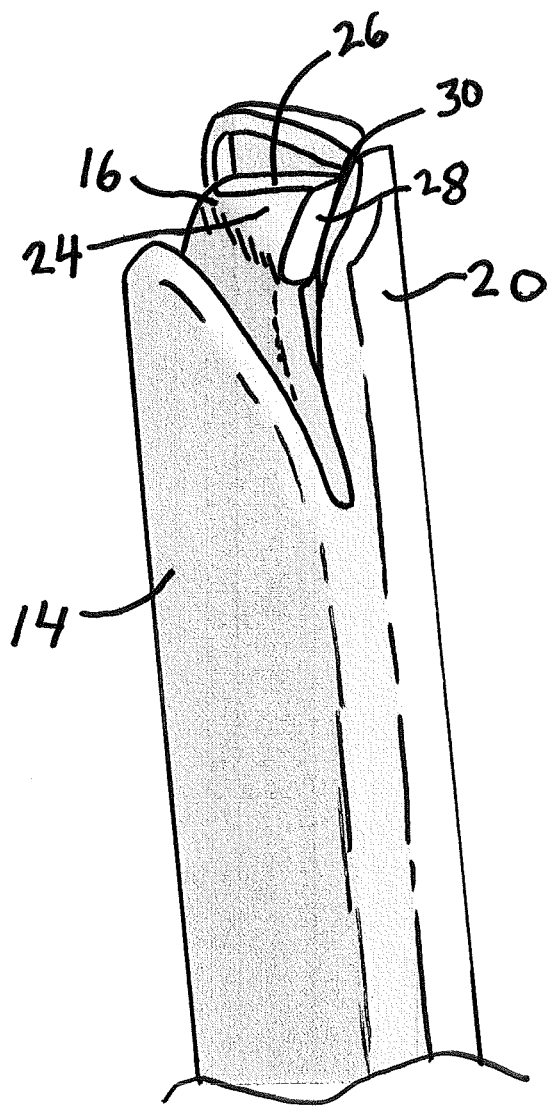
FIG. 2 is a perspective view of the distal tip of the instrument of FIG. 1, showing a shroud disposed over the cutting tip.

Referring now to FIG. 1, instrument 10 includes of a handle 12 and a distal shaft 14 that holds a blade or cutter 16. There is a knob 18 on the handle that activates the rotation of the cutter 16. As shown in FIG. 2, there is also a shroud 20 that covers the cutting edge of the cutter 16 to ensure safe insertion and withdrawal.

Figure 3:
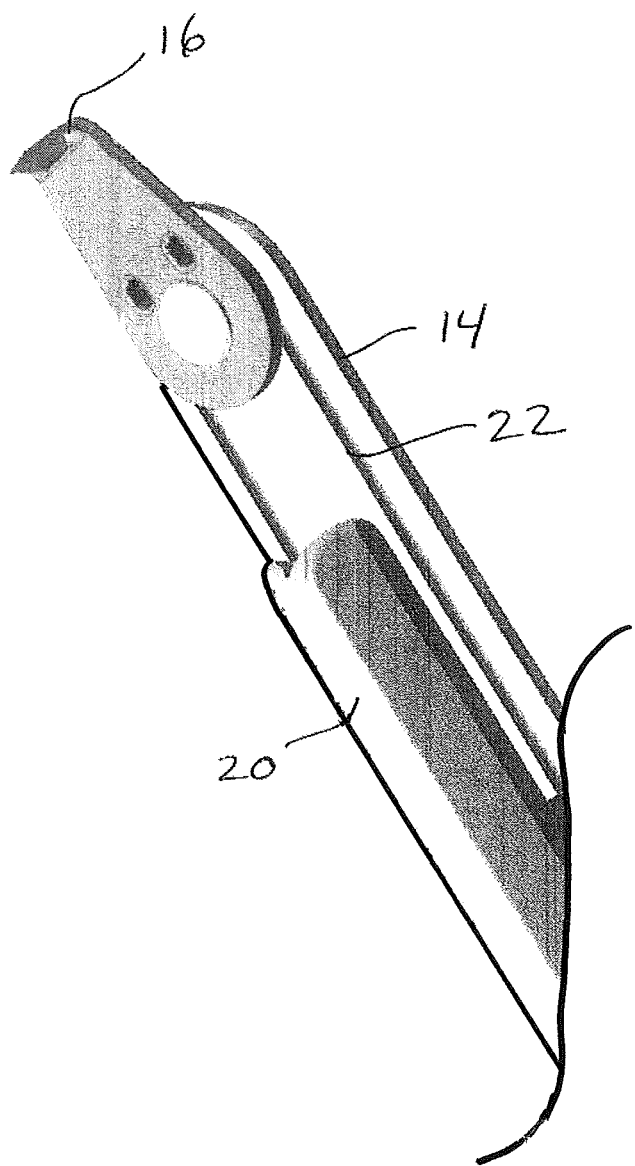
FIG. 3 is a perspective view of the underside of the distal tip of the instrument of FIG. 1, showing the shroud retracted to expose the cutting blade.

Referring now to FIG. 3, a pliable body 22, which can be a string, wire, rod, band, cable, or the like, is attached to the cutter and also to the rotating knob 18 in the handle. As the surgeon turns the rotating knob, one side of pliable body 22 is pulled and it pulls the cutter 16 past 180° in one direction. When the surgeon turns the rotating knob 18 in the opposite direction, the surgeon can get cutter 16 back to 0° rotation (the starting point) and continue 180° past the other direction to provide a full 360 degree plus cut motion. The pliable body is affixed to the rotating knob so that as the surgeon rotates the knob 18, the blade of cutter 16 will rotate accordingly. The knob 18 is intuitive and easy to use. The surgeon will be able to turn the knob with a gentle movement of the thumb or forefinger, depending upon grip style, thus minimizing movement of the instrument inside the eye. In one method of use, it is contemplated that the device may be grasped between the thumb and forefinger in the same manner as a scalpel, pen or pencil is held, with either the thumb or forefinger easily positioned against the knob 18 when rotation is desired to effectuate the desired motion of the knob 18 and, hence the blade of cutter 16.

With continuing reference to FIG. 3, the part of the device that enters the eye (the distal shaft or blade carrier 14, the blade of cutter 16 and the shroud 20) is approximately 2 mm wide. The thickness, including the shroud, is approximately 1½ mm thick. This will allow the instrument to enter the eye through the 2-3 mm limbal or corneal incision, with no distortion of the wound. Those skilled in the art will readily appreciate that these dimensions are exemplary, and that they can be varied within a suitable range, without departing from the spirit and scope of the invention.

The majority of the instrument 10 is advantageously made out of transparent plastic for visualization of location and for ease of performance, however, any other suitable materials can be used as will be appreciated by those skilled in the art. There can be a mark on the transparent instrument that can allow the surgeon to center the instrument in the center of the eye. This can allow for the creation of a concentric capsulotomy. This can also facilitate proper placement of the IOL within the capsule.

The cutting blade of cutter 16 can be made of any suitable medical grade cutting material, such as medical cutting-grade stainless steel. The shroud 20 is slidable along the distal shaft from a first position covering the cutting blade (see FIG. 2) to a second position revealing the cutting blade for use (see FIGS. 1 and 3).

The blade is advantageously angled inward toward the center of the eye, i.e., the axis of rotation of the blade, such that where it cuts the anterior capsule, the angle formed between the blade and the axis of blade rotation blade is less than 90°, in order to further decrease the risk of radial tears. However, those skilled in the art will readily appreciate that the blade could also be angled differently, e.g., parallel to the axis of rotation, without departing from the spirit and scope of the invention.

The cutting edge of the blade of cutter 16 has cutting facets for piercing initially, and then allowing for cutting in both clockwise and counterclockwise directions. As shown in FIG. 2, the blade tip 24 is substantially perpendicular to the shaft (subject to the advantageous blade angulation described above) and has a substantially triangular shape with angled cutting edges 26, 28 and a sharp tip 30.

The length of the turning blade of cutter 16 can be varied such that instruments constructed in accordance with instrument 10 can be made for a variety of predetermined cutting diameters. For example, an ACR (anterior capsule remover) instrument 10 which creates a 3 mm diameter capsulotomy could be available for patients with smaller pupils. An ACR that could create a 4 or a 5 mm diameter capsulotomy, or any other suitable size, can also be made available.

Figure 4:
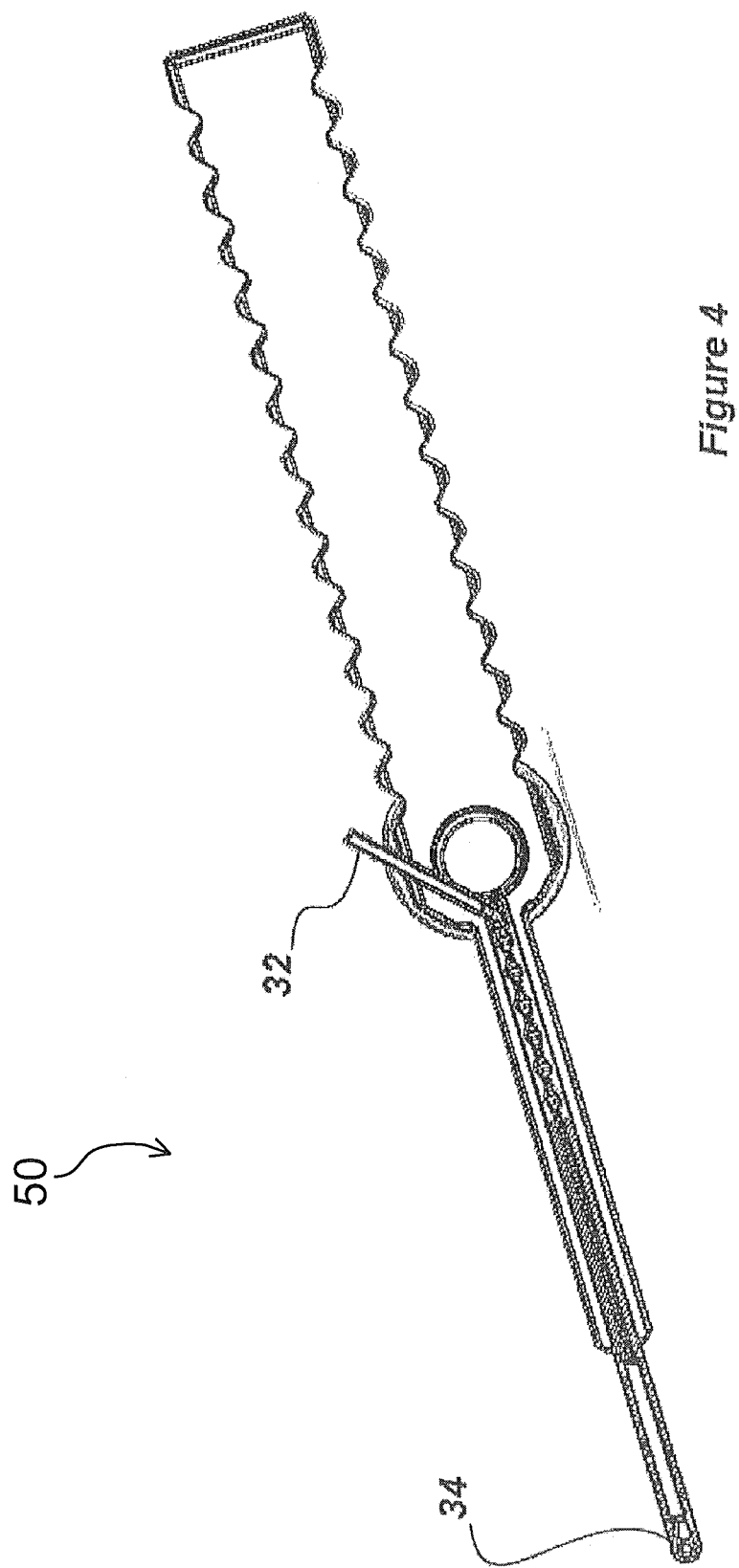
FIG. 4 is a top view of another exemplary embodiment of an instrument constructed in accordance with the present invention, showing a catheter for injecting material into the eye.

When the capsulotomy procedure is completed, the circular piece of the anterior capsule that has been cut by this instrument could be removed from the eye by placing it between the blade tip and the retracting sheath, pulling the sheath down to grasp the piece of capsule, and gently pulling it (along with the instrument) out of the eye. Alternatively, a forceps could be placed in the eye at the paracentesis site or at the limbal or corneal incision site, and then used to grasp and remove the cut piece of anterior capsule. The instrument 10 can also include a suction catheter that can be used to remove the circular piece of the anterior capsule that has been cut. As shown in FIG. 4, another exemplary instrument 50, similar in most respects to instrument 10 described above, can also be adapted to have a catheter 32 and an orifice 34 such that viscoelastic material could be injected into the eye through this instrument, if desirable.

In use, the ACR instrument 10 is inserted, for example, through the limbal incision with the shroud 20 covering the cutting blade. Once the distal tip of the instrument is positioned over the portion of the anterior lens capsule to be opened, the shroud 20 is slid back along the shaft to reveal the cutting tip. The sharp tip of the cutting tip is urged against the anterior lens capsule to penetrate the capsule and initiate the incision. With the blade penetrating the capsule, knob 18 is rotated in a first direction to impart tension to the pliable body 22 so that blade of cutter 16 is caused to rotate in a first direction about the blade axis of rotation (which may be defined by the axis of a post to which the cutter 16 is mounted—see FIG. 3, for example) to effectuate a curved cut in the anterior lens capsule. In the preferred embodiment a stop is provided such that the blade rotates through an angle slightly greater than 180° (e.g., 190°), and then the knob 18 is rotated in the opposite direction so that the string imparts tension to the blade to rotate the blade in the opposite direction until the blade returns to its initial, start or neutral position. Rotation of the knob 18 in the second direction is continued so that the blade continues to rotate past the initial or neutral position and rotates through an angle of rotation sufficient to complete the cut with the initial cut in the opposite direction. That is, the blade rotates in the second direction approximately 180° or slightly greater (e.g., 190°) so the curved incisions made by rotating the blade in the first and second directions meet to form a complete cut. The cut out portion of the anterior lens capsule may then be removed in a known manner.

As will be appreciated, the dual cutting edges 26 and 28 facilitate two-directional cutting by providing a cutting blade on each side of the cutting tip. It is believed that this configuration, together with the pliable body 22 interaction between the blade and the knob 18, advantageously provide a high degree of control for the surgeon during the delicate process of cutting the anterior lens capsule. It is also contemplated, however, that the blade can be configured to rotate in only a single direction in a full circular arc, in which case only a single cutting edge is required on the cutting tip. Also, while the tension band or string approach is preferred, it is contemplated that the pliable body can be sufficiently rigid to impart motion to the blade through compression forces rather than tension. It is also contemplated that multiple turns of the pliable body 22 about the base of the knob 18 and/or the blade hub could increase friction between the pliable body 22 and the knob 18 or blade, respectively, in a capstan effect which may provide even greater control or "feel" to the surgeon during the cutting process. Gear teeth and other configurations of interaction between the pliable body 22 (which can include string, wire, a belt, cable, a band, and/or the like) and the knob 18 and/or the blade are also within the scope of this disclosure.

Since the ACR instrument 10 may easily be placed through a typical 2 mm conical or limbal incision that is typical of cataract surgery, the use of the ACR instrument 10 requires no modification to accepted surgical approaches to the treatment of cataracts. Due to the rotating knob 18 being capable of being turned with a gentle movement of the thumb, this instrument 10 allows for less mechanical trauma at the insertion site into the anterior chamber. In this way, the instrument 10 reduces potential postoperative scarring. By eliminating distortion of the wound that occurs with other capsulotomy techniques, it may also eliminate the potential need for a suture to close a larger wound into the anterior chamber. The ACR instrument 10 creates a unique, one-pass-technique capsulotomy. The insertion of this device, with the sheath on, reduces the risk of potential insertion trauma. The advantageously accurate placement of the capsulotomy ensures ensure better IOL function. Removal of the instrument 10 with the sheath on also reduces risk to other ocular structures during withdrawal of the instrument 10. This instrument 10 can be used in a safe, reliable and consistent fashion. Additionally, the surgeon can achieve a capsular opening of optimal shape and predetermined size, specific to the exact needs of each patient.

Figures 5, 5A:
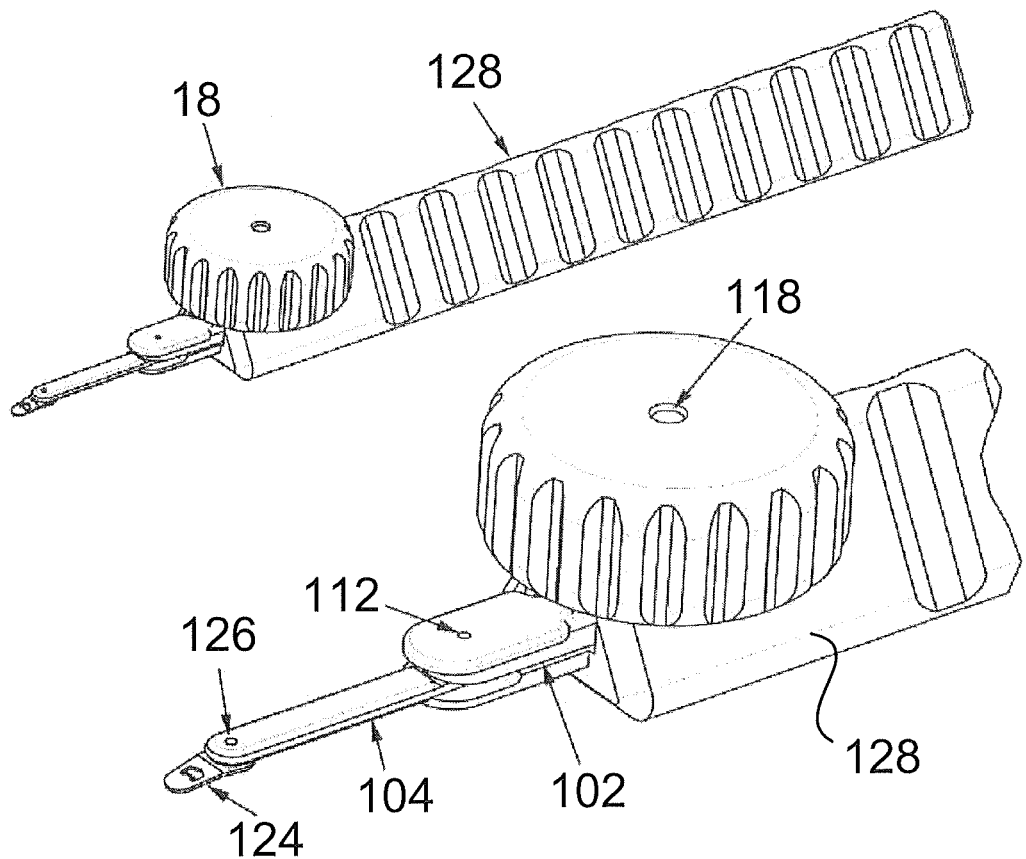
FIG. 5 is a perspective view of another exemplary embodiment of an instrument constructed in accordance with the present invention, showing the handle with triangular cross-section.
FIG. 5A is a close up perspective view of the distal end of the device of FIG. 5, showing the blade of the instrument.
Figure 6:
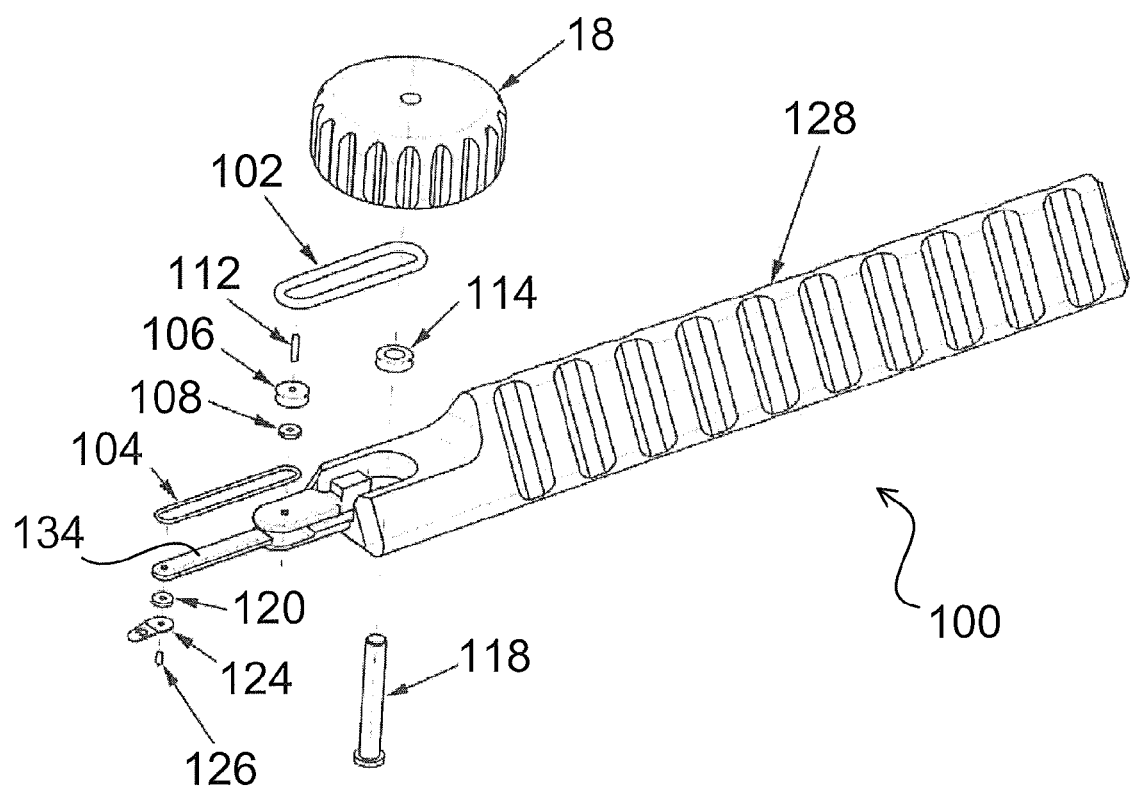
FIG. 6 is an exploded perspective view of the instrument of FIG. 5, showing the drive o-ring.

Referring now to FIGS. 5, 5A, and 6, assembly of an ACR instrument is described in the exemplary context of another embodiment of an ACR instrument 100. Instrument 100 is similar to instrument 10 described above, but has a handle 128 with a generally triangular cross-sectional profile, rather than the generally rectangular profile of the handle 12 of instrument 10. The drive o-ring 102 and the blade o-ring 104 are slid over the drive pulley 106 and blade pulley 108. The drive pulley 106 is stacked on top of blade pulley 108. The stacked pulleys 106 and 108 are then slid into the holder's drive pocket 110, identified in FIG. 12C. The drive pin 112 is slid through the roof of the holder's drive pocket 110, through the center holes of drive pulley 106 and blade pulley 108, and then pressed into the floor of the holder's drive pocket 110. The two pulleys 106 and 108 should freely spin.

The thumbwheel pulley 114 is placed into the holder's thumbwheel pocket 116, identified in FIG. 12B. The drive o-ring 102 is then stretched over the thumbwheel pulley 114. The thumbwheel pin 118 is slid through the floor of the holder's thumbwheel pocket 116 and the center hole of thumbwheel pulley 114. The thumbwheel 18 is pressed onto the thumbwheel pin 118. The thumbwheel sub-assembly should freely spin. The thumbwheel 18 can also be slid onto the thumbwheel pin 118 then held on by a set-screw through the sidewall of the thumbwheel pressing on the side of the thumbwheel pin 118.

The blade pulley 120 is placed inside the holder's blade pulley pocket 122, identified in FIG. 12*d*. The blade 124 is then located below the floor of the blade pulley pocket 122. The blade pulley pin 126 is pressed through the center hole of the blade 124, slid through the floor of the blade pulley pocket 122, pressed through the center hole of the blade pulley 120 and slid through the roof of the blade pulley pocket 122. The blade o-ring 104 can then be stretched over the blade pulley 120. The blade 124 and blade pulley 120 should spin freely. The blade pin 126 can also be assembled through the roof of the blade pulley pocket 122 first then pressed and slid through the components as previously described.

Figure 6A:
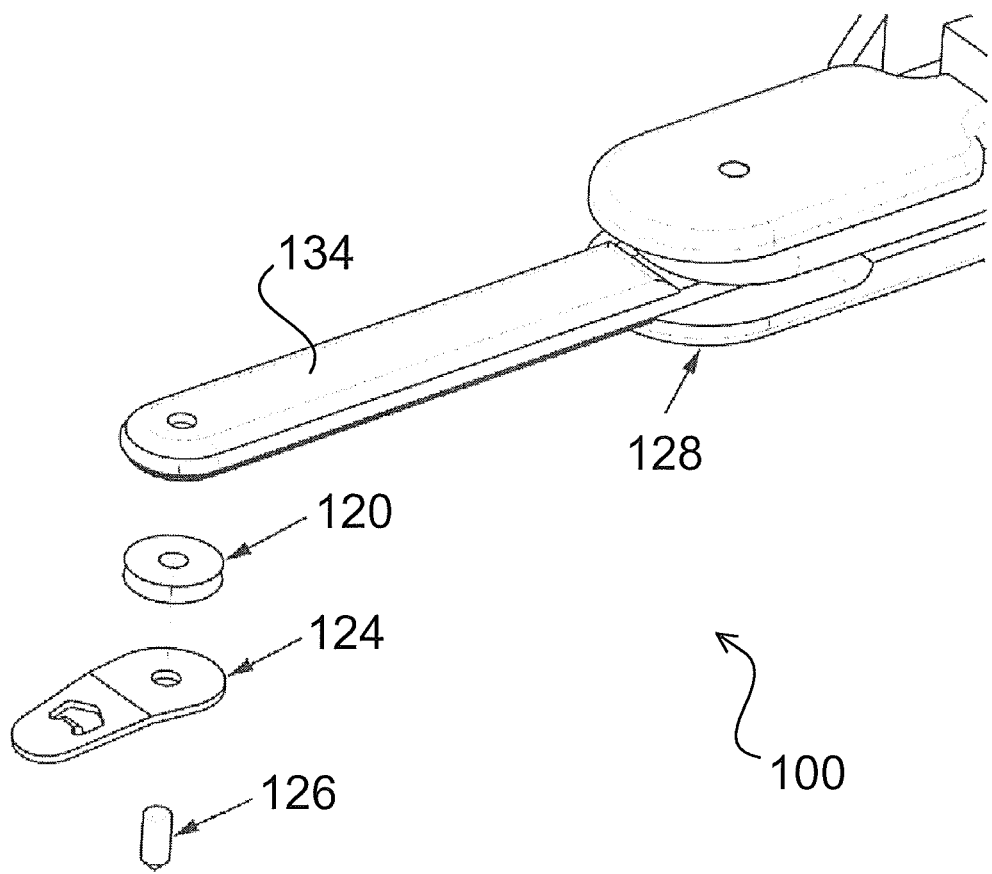
FIG. 6A is a close up perspective view of a portion of the instrument of FIG. 6, showing the blade and associated blade pulley.
Figures 9A, 9B:
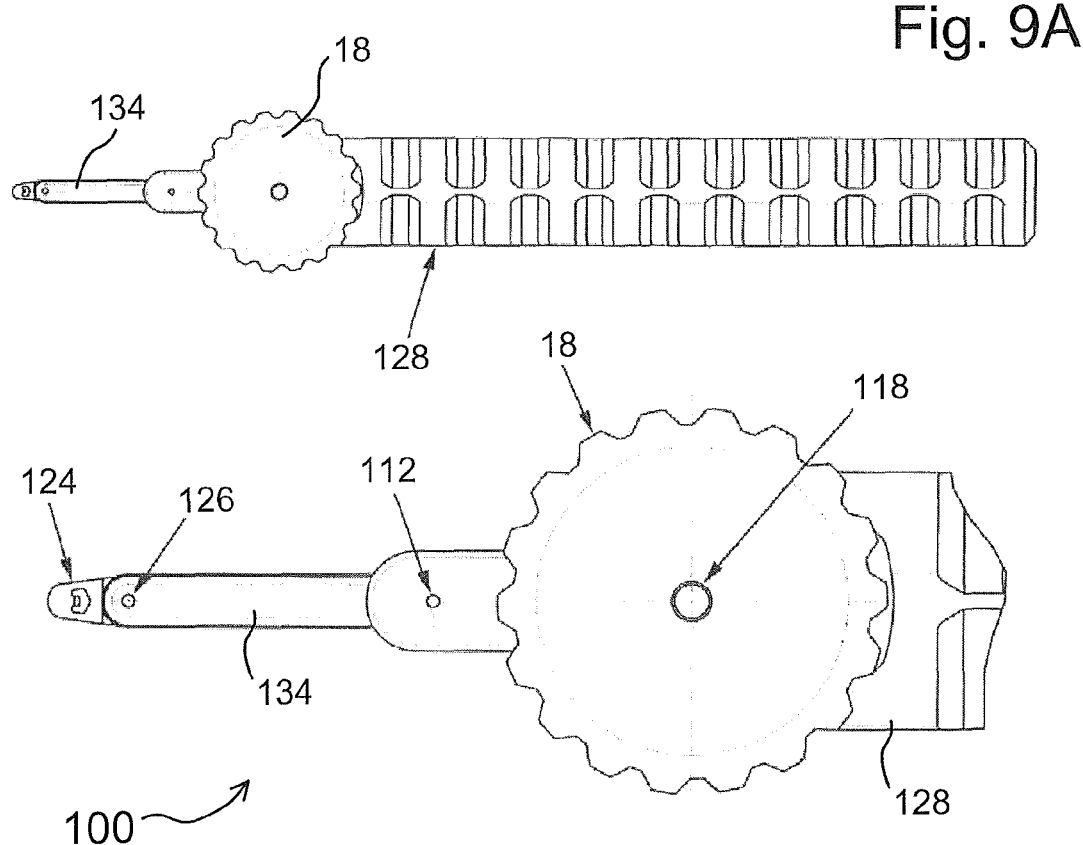
FIGS. 9A-9B are top views of the instrument of FIG. 5, showing the handle and thumbwheel portions, respectively.
Figure 10:
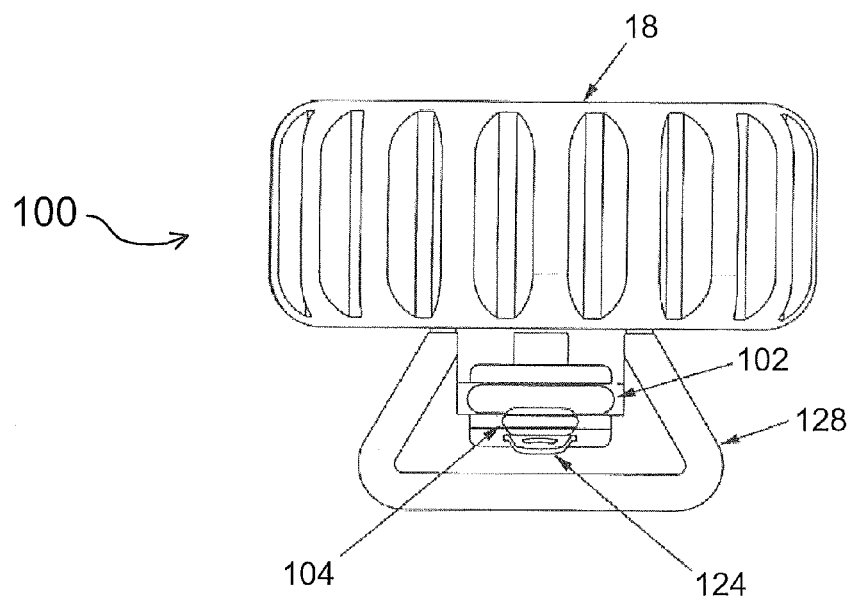
FIG. 10 is a front elevation view of the instrument of FIG. 5, showing the blade, driver o-ring, and blade o-ring in relation to the thumbwheel and holder.
Figure 11:
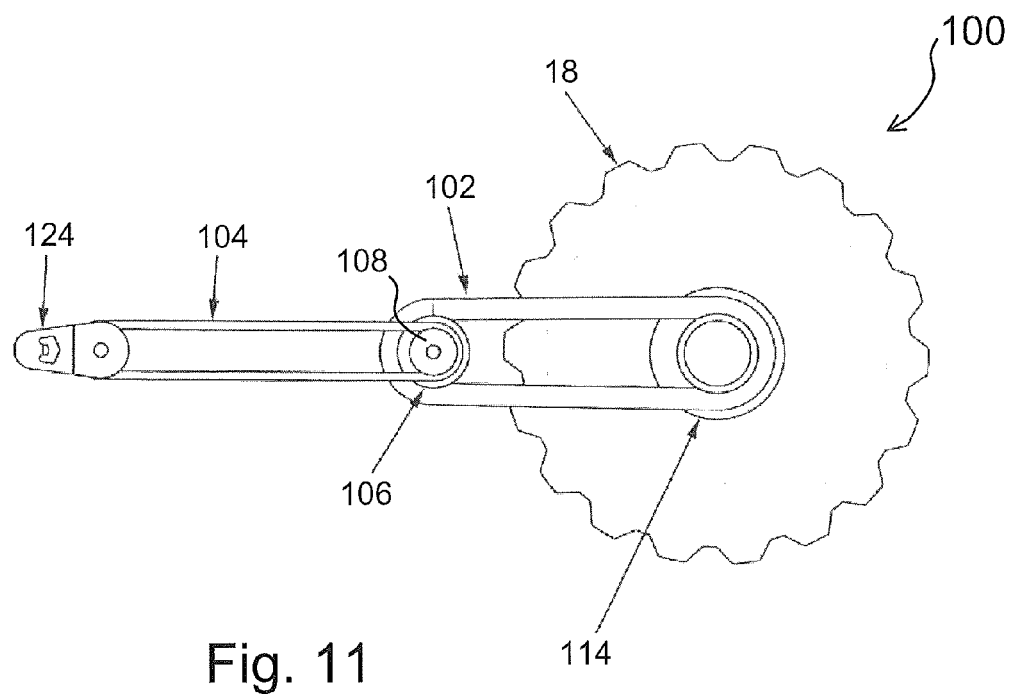
FIG. 11 is a bottom view of the pulley system of the instrument of FIG. 5, showing the supporting structure removed.
Figure 15A:
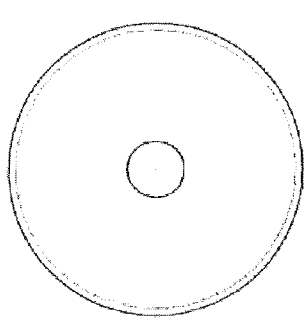
FIGS. 15A-15C are plan, perspective, and side elevation views, respectively, of the drive pulley of the instrument of FIG. 5.
Figure 15B:
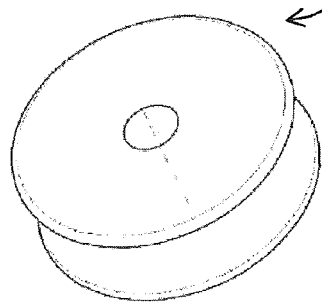
Figure 15C:
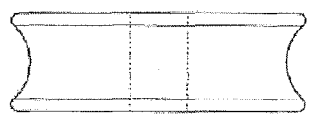
Figure 16A:
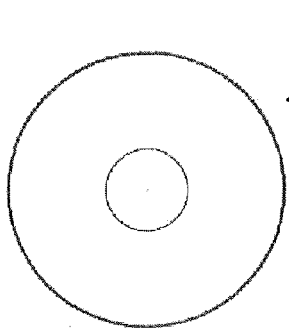
FIGS. 16A-16C are plan, perspective, and side elevation views, respectively, of the blade pulleys of the embodiment of FIG. 5.
Figure 16B:
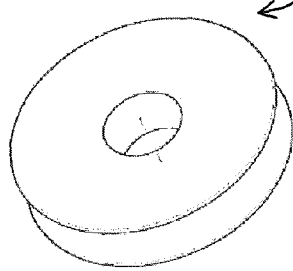
Figure 16C:
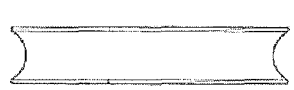
Figure 17A:
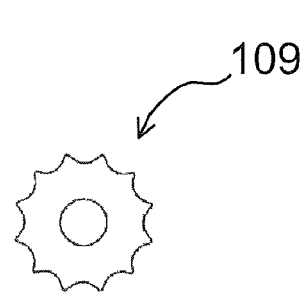
FIGS. 17A-17F are respective plan and side elevation views for each of three respective variations of pulleys with teeth.
Figure 17C:
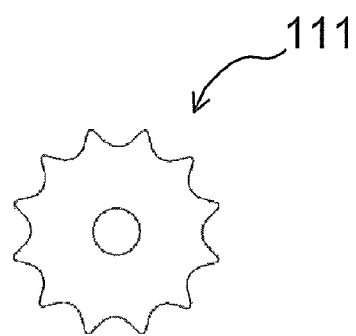
Figure 17E:
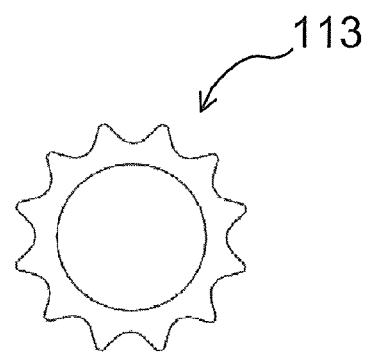
Figure 17B:
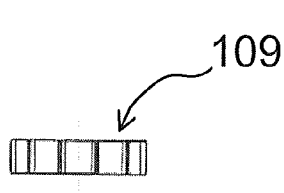
Figure 17D:
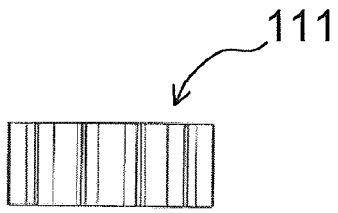
Figure 17F:
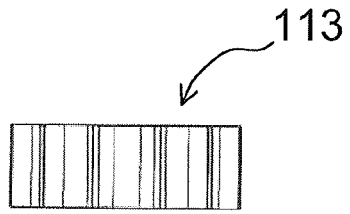

FIG. 6A shows distal shaft 134 and related components separated from one another in a close up view. FIGS. 7A-7C show a series of three increasingly close up cross-sectional views of instrument 100 with the components described above assembled to handle 128. FIGS. 8A and 8B similarly show two increasingly close up views of instrument 100 assembled as described above, as viewed from the side as in FIGS. 7A-7C but not in cross-section. FIGS. 9A and 9B show two increasingly close up views of instrument 100 from above, i.e., looking towards the circular face of the thumbwheel or knob 18, showing the components described above assembled. FIG. 10 shows assembled instrument 100 as viewed along its longitudinal axis, looking towards blade 124. FIG. 11 shows components of the mechanism of instrument 100, including the thumbwheel or knob 18 connected to the thumbwheel pulley 114, which is connected to drive pulley 106 via drive o-ring 102. As shown in FIG. 11, drive pulley 106 connects to blade pulley 108, which is in turn connected to blade 124 via blade o-ring 104 and blade pulley 120 (not shown in FIG. 11, but see FIG. 6). FIG. 12A shows grips 129 of handle 128 for increasing handle-ability of instrument 100. FIGS. 12C and 12D show increasingly close up views of shaft 134 without the pulley mechanism fully assembled. FIGS. 12C and 12D also show the drive o-ring groove 111 and the blade o-ring groove 123 for accommodating the respective o-rings. FIGS. 13A, 13C, and 13E show thumbwheel or knob 18 from above, from the side, and from below, respectively, and FIGS. 13B, 13D, and 13F show knob 18 in perspective from above, from the side with the center hole shown, and in perspective from below, respectively.

With continued reference to FIGS. 5-6A, the basic operation of the ACR instrument 100 will now be described in further detail. The user grasps the holder and rotates the thumbwheel (knob 18). The thumbwheel is directly coupled to the thumbwheel pulley 114 by being press-fit onto the thumbwheel pin 118. The thumbwheel and thumbwheel pulley 114 spin the stretched drive o-ring 102 causing the drive pulley 106 to spin. The drive pulley 106 and blade pulley 108 are directly coupled to each other. As the drive pulley 106 and blade pulley 108 are spun by the drive o-ring 102, they and the stretched blade o-ring 104 cause the blade 124 and blade pulley 120 to spin.

The circumference of the drive pulley 106 is about 10% smaller than the circumference of the thumbwheel pulley 114. This causes the drive pulley 106 and subsequently the blade 124 to rotate about 10% more than the thumbwheel. For every 360° of rotation of the thumbwheel, the blade 124 will rotate 396°. Both blade pulleys 108 and 120 are identical. FIGS. 17A-17F show three different pulleys 109, 111, and 113 that can be used, in which the "c" shaped wall on any of the respective pulleys 106, 108, 114, and 120 shown in FIGS. 14A-16C could be replaced with a straight wall with teeth located about the circumference. While the devices described herein have been described in an exemplary context of about 360° cutter rotation, those skilled in the art will readily appreciate that the cutter rotation can be configured to be, for example, about 330°, about 400°, or any other suitable cutter rotation range.

Figure 20:
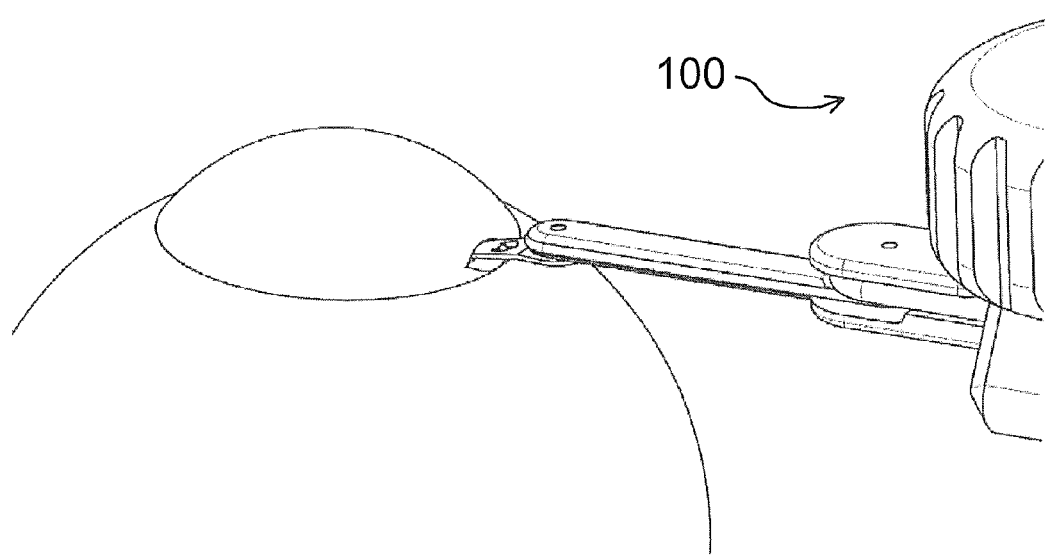
FIG. 20 is a perspective view of the instrument of FIG. 5, showing the introducer portion of the blade passing through the incision.
Figure 21:
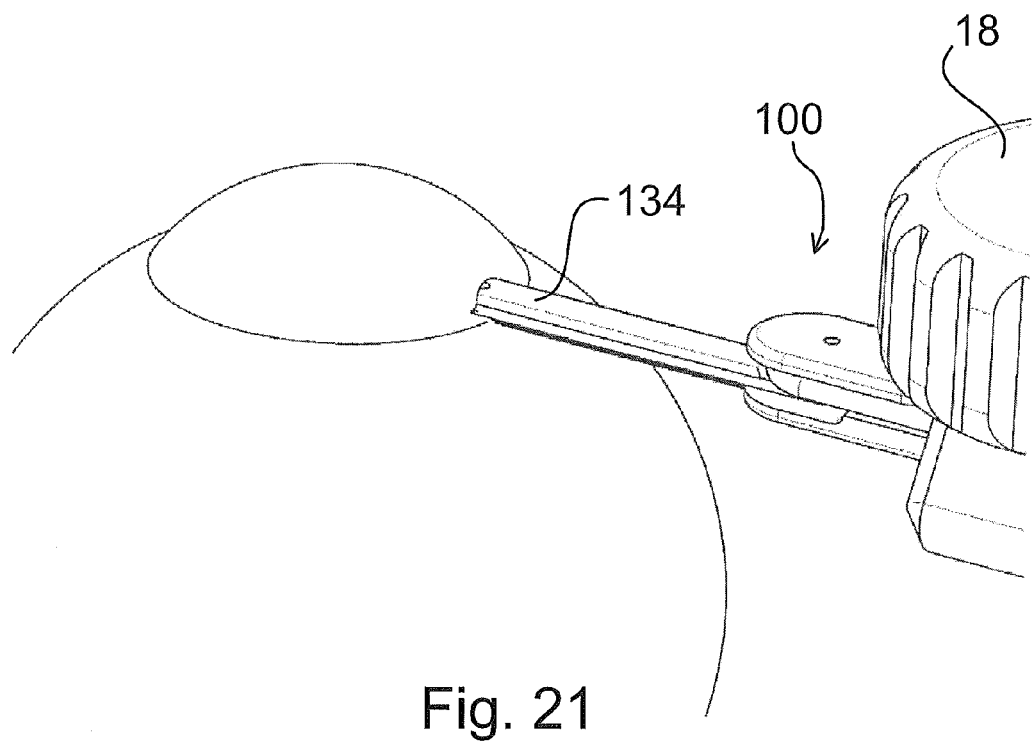
FIG. 21 is a perspective view of the instrument of FIG. 5, showing the blade passed through the incision.

Referring now to FIGS. 19-23, an exemplary operation of ACR instrument 100 in surgery will now be described. As shown in FIG. 19, the user creates a 2-3 mm incision at the limbus of the eye. The user approaches the eye with the ACR instrument 100. The instrument includes of a handle 128 (or "holder") and a distal shaft 134 that holds a blade 124 or cutter. The introducer 130 of blade 124 shown in FIGS. 18A-18G, is inserted into the incision. Lifting up the roof of the incision creates clearance so that the sharp edge 132 (see FIGS. 18A-18G) will not damage the incision's floor, as the blade 124 and then the distal shaft 134 are introduced into the eye's anterior chamber, as shown in FIGS. 20 and 21, respectively. In other embodiments, such as instrument 10 described above, a retractable cover could be in place over the blade for this same basic purpose. In another different approach, a shield (such as a hollow tube-like apparatus) could be introduced into the eye first. The ACR instrument 100 could then be slid through this inserter, and introduced into the eye in a protected fashion.

Figure 22:
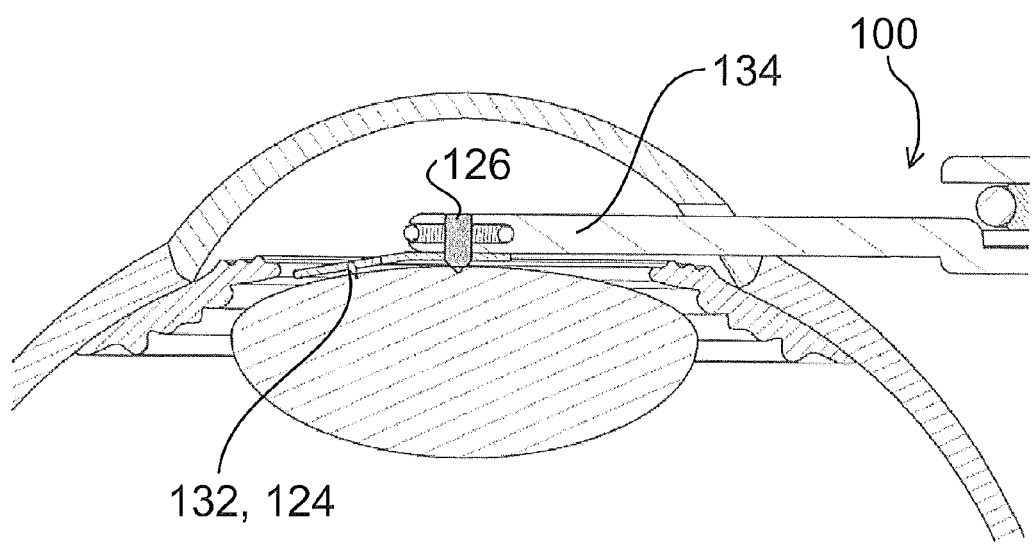
FIG. 22 is a cross-sectional side elevation view of the instrument of FIG. 5, showing the distal tip within the anterior capsule positioned to perform capsulotomy.

Referring now to FIG. 22, after the distal shaft 134 has been introduced through the incision, the ACR instrument 100 is advanced into the anterior chamber until the blade pin 126 is centered over the eye's lens. The user will then seat the blade pin 126 and the sharp edge 132 of the blade 124 through the anterior capsule. The blade pin could instead have a blunt bottom and just sit on top of the capsular bag.

Figure 23:
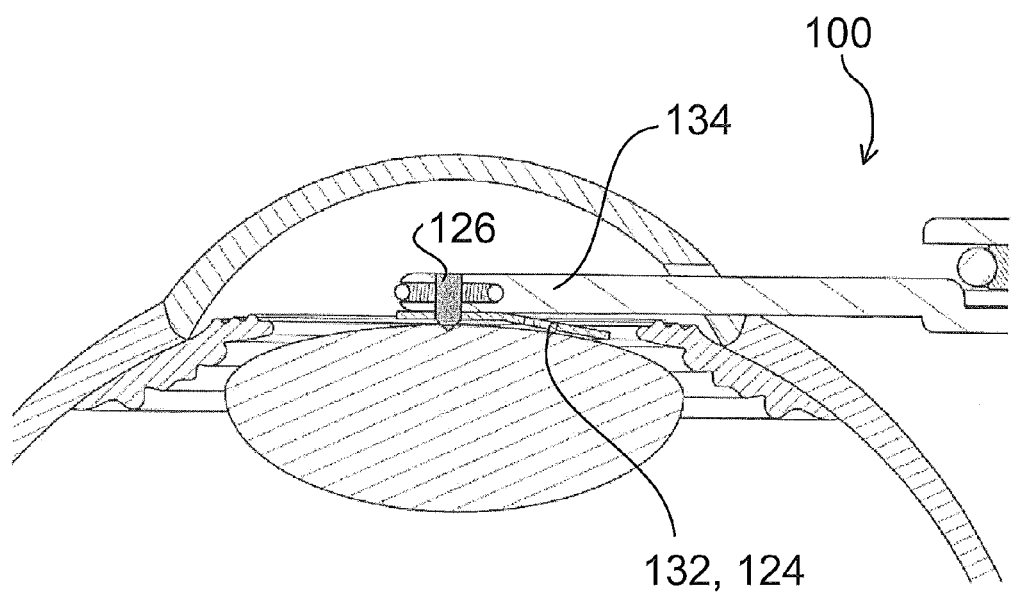
FIG. 23 is a cross-sectional side elevation view of the embodiment of FIG. 5, showing the blade rotated through an arc of 180° from the position shown in FIG. 22.

Referring now to FIGS. 22 and 23, with the blade pin 126 and sharp edge 132 of blade 124 in place, the user rotates the thumbwheel 18 at least one full turn. FIGS. 22 and 23 show blade 124 in different positions while cutting. The blade 124 will rotate creating a complete circular cut into the capsular bag. This will occur because of the o-rings attached to the blade and also to the rotating knob in the handle, as described above. As the surgeon turns the rotating knob, the blade 124 will rotate accordingly. The thumbwheel or knob 18 is intuitive and easy to use and control. The surgeon will be able to turn the knob 18 with a gentle movement of the thumb or forefinger, depending upon grip style, thus minimizing movement of the instrument inside the eye. In one method of use, it is contemplated that the device may be grasped between the thumb and forefinger in the same manner as a scalpel, pen or pencil is held, with either the thumb or forefinger easily positioned against the knob when rotation is desired to effectuate the desired motion of the knob 18 and, hence the blade 124.

The part of the device that enters the eye (the distal shaft 134 or blade carrier) is approximately 2 mm wide. The thickness will be approximately 1½ mm thick. This will allow the instrument to enter the eye through the 2-3 mm limbal or corneal incision, with no distortion of the wound. Those skilled in the art will readily appreciate that these dimensions can be varied within any suitable limits without departing from the spirit and scope of the invention.

The blade 124 is preferably angled inward toward the center of the eye, i.e., the axis of rotation of the blade, such that where it cuts the anterior capsule, the angle formed between the blade and the axis of blade rotation blade is less than 90°, in order to further decrease the risk of radial tears, as described above. The cutting edge 132 has cutting facets for piercing initially, and then allow for cutting in both clockwise and counterclockwise directions, as described above. As shown in the Figures, e.g., FIGS. 22-23, the blade tip of cutting edge 132 is substantially perpendicular to the distal shaft 134 (subject to the preferred blade angulation described above) and has a substantially triangular cross-sectional shape with angled cutting edges and a sharp tip.

The length of the turning blade 124 of the instrument can vary such that instruments could be available for a variety of predetermined diameters. For example, an ACR instrument which creates a 3 mm diameter capsulotomy could be available for patients with smaller pupils. An ACR that could create a 4 or a 5 mm diameter capsulotomy could also be available, or any other suitable size, as described above.

When the capsulotomy procedure is completed, a forceps could be placed in the eye at the paracentesis site or at the limbal or corneal incision site, and then used to grasp and remove the cut piece of anterior capsule. It is also contemplated that the ACR instrument used could also have a suction catheter that could be used to remove the circular piece of the anterior capsule that has been cut, as described above. The ACR instrument used can also be adapted to have a catheter 32 and an orifice 34 such that viscoelastic material could be injected into the eye through this instrument, if desirable (as in ACR instrument 50 shown in FIG. 4).

There are several reasons why instruments and methods described herein provide an improvement over traditional instruments and procedures. First, the ACR instruments described herein decrease the time and effort associated with the capsulotomy procedure by allowing the surgeon to quickly and efficiently create a symmetric capsulotomy, with substantially reduced risk of capsular tears. Second, by obtaining a centered, symmetric removal of the anterior capsule, these instruments prevent increased operative time associated with the complications of capsular tears. Also, the complications and lesser results associated with radial capsular tears can be eliminated, saving cost by avoiding additional treatment while improving the quality of patients' final visual outcomes.

Since the ACR instruments described herein may easily be placed through a 2 mm corneal or limbal incision that is typical of cataract surgery, the use of these ACR instruments requires no modification to accepted surgical approaches to the treatment of cataracts. Since the rotating knob can be turned with a gentle movement of the thumb, the instruments described herein allow for less mechanical trauma at the insertion site into the anterior chamber. In this way, the instruments reduce potential postoperative scarring. By eliminating distortion of the wound that occurs with other capsulotomy techniques, it may also eliminate the potential need for a suture to close a larger wound into the anterior chamber. The ACR instruments and methods described herein create a unique, one-pass-technique capsulotomy. Accurate placement of the capsulotomy would ensure better IOL function. These instruments and methods can be used in a safe, reliable and consistent fashion, and the surgeon can achieve a capsular opening of optimal shape and predetermined size, specific to the exact needs of each patient.

While the devices and methods above have been described above in the exemplary context of capsulotomies, those skilled in the art will readily appreciate that the invention can be configured and practiced in any other suitable procedure without departing from the spirit and scope of the invention. For example, it is contemplated that a cutting device in accordance with the invention could be configured for use during arthroscopies for making arcuate (possibly less than 360° and/or of variable radius) cuts in the meniscus and/or articular cartilage, or for use in endoscopies for removal of polyps, or any other procedures where a precise cut is needed.

The methods and systems of the present invention, as described above and shown in the drawings, provide for devices and methods with superior properties including improved capsulotomies. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. A cutting device comprising:
   a handle;
   a shaft extending from the handle, the shaft rotatably supporting a cutting blade;
   an actuator operatively connected to rotate the cutting blade, the actuator including an actuator pulley mounted in a proximal portion of the shaft, a first blade pulley mounted in the proximal portion of the shaft and operatively connected for rotation with the actuator pulley, and a second blade pulley mounted in a distal portion of the shaft, wherein the distal portion of the shaft has a smaller cross-sectional area than that of the proximal portion of the shaft and wherein the distal portion of the shaft is configured and dimensioned for insertion into the anterior chamber of the eye, and wherein the cutting blade is a capsulotomy blade rotatably mounted at the distal end of the shaft operatively connected for rotation with the second blade pulley; and
   a knob mounted operatively connected to the handle, wherein the knob is operatively connected to the actuator pulley so that rotation of the knob rotates the capsulotomy blade, and wherein the knob is operatively connected to the capsulotomy blade by a first elastomeric ring connecting a knob pulley operatively connected for rotation with the knob to the actuator pulley, and by a second elastomeric ring connecting the first blade pulley to the second blade pulley, wherein the cross-sectional area of the second elastomeric ring is smaller than that of the first elastomeric ring.

2. The device of claim 1, further comprising a shroud movable along the shaft for selectively covering or exposing the capsulotomy blade.

3. The device of claim 1, wherein the capsulotomy blade includes an introducer section distal to a downwardly projecting cutting blade.

4. The device of claim 1, wherein the second blade pulley is mounted at a distal end of the shaft, and the capsulotomy blade is mounted relative to the second blade pulley such that rotation of the blade pulley rotates a cutting edge of the capsulotomy blade through an arc.

5. The device of claim 4, further comprising a blade pin disposed on the axis of rotation of the blade.

* * * * *